(12) United States Patent
Lal et al.

(10) Patent No.: US 12,319,567 B2
(45) Date of Patent: Jun. 3, 2025

(54) GHz-THz ULTRASONICS AND OPTICS FOR NEUROTECHNOLOGY DEVICES, METHODS, AND APPLICATIONS

(71) Applicant: CORNELL UNIVERSITY, Ithaca, NY (US)

(72) Inventors: Amit Lal, Ithaca, NY (US); Chris Xu, Ithaca, NY (US); Ankur Singh, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 765 days.

(21) Appl. No.: 17/058,237

(22) PCT Filed: May 23, 2019

(86) PCT No.: PCT/US2019/033688
§ 371 (c)(1),
(2) Date: Nov. 24, 2020

(87) PCT Pub. No.: WO2019/226862
PCT Pub. Date: Nov. 28, 2019

(65) Prior Publication Data
US 2021/0187329 A1    Jun. 24, 2021

Related U.S. Application Data

(60) Provisional application No. 62/675,973, filed on May 24, 2018.

(51) Int. Cl.
*A61N 7/00* (2006.01)
*B06B 1/06* (2006.01)
(Continued)

(52) U.S. Cl.
CPC ............ *B81C 1/00238* (2013.01); *A61N 7/00* (2013.01); *B06B 1/0622* (2013.01);
(Continued)

(58) Field of Classification Search
CPC .................................................. B81C 1/00238
See application file for complete search history.

(56) References Cited

U.S. PATENT DOCUMENTS 6,515,271 B1    2/2003   Shimizu
2007/0092958 A1  4/2007   Syed et al.
(Continued)

FOREIGN PATENT DOCUMENTS

CN          202977650 U       6/2013

OTHER PUBLICATIONS

International Search Report and Written Opinion for International Application No. PCT/US2019/033688 dated Aug. 12, 2019; 9 pages.
(Continued)

*Primary Examiner* — Joseph M Santos Rodriguez
(74) *Attorney, Agent, or Firm* — Barnes & Thornburg (57) ABSTRACT

An integrated GHz ultrasonic neuro-cognitive system including a chip-cyborg having a network of biological neurons that forms a biological information processor, which can be controlled by electronics, optics, and GHz ultrasonic beams. In one example, the chip-scale microsystem includes a CMOS chip with RF CMOS and piezoelectric thin film transducers that can generate GHz ultrasonic waves, which can be phased to form narrow beams, achieving significant ultrasonic intensity to affect neurons. With a sufficient number of ultrasonic pixels, the focal point of the beam can be narrow enough to focus effect specific section of a neuron to enhance or decrease synaptic weights owing to ultrasonic radiation forces and acoustic streaming.

22 Claims, 9 Drawing Sheets

(51) Int. Cl.
*B81C 1/00* (2006.01)
*H10N 30/853* (2023.01)
*H10N 39/00* (2023.01)
*A61B 5/00* (2006.01)

(52) U.S. Cl.
CPC ........... *H10N 30/853* (2023.02); *H10N 39/00* (2023.02); *A61B 5/0084* (2013.01); *A61N 2007/0026* (2013.01); *A61N 2007/0047* (2013.01)

(56) References Cited

U.S. PATENT DOCUMENTS

| | | |
|---|---|---|
| 2007/0152249 A1 | 7/2007 | Lim |
| 2014/0355381 A1 | 12/2014 | Lal et al. |
| 2017/0247250 A1 | 8/2017 | Otte et al. |

OTHER PUBLICATIONS

Schmalz, K. et al. "A 120 GHz Dielectric Sensor in SiGe BiCMOS," IEEE Microwave and Wireless Components Letters, vol. 23, No. 1, Jan. 1, 2013, pp. 46-48.

GHz-THz ULTRASONICS AND OPTICS FOR NEUROTECHNOLOGY DEVICES, METHODS, AND APPLICATIONS

CROSS REFERENCE

This application is a U.S. National Phase filing of International Application No. PCT/US19/33688 filed May 23, 2019, which claims priority to U.S. Provisional Patent Application Ser. No. 62/675,973, filed on May 24, 2018 and Entitled "Ghz-Thz Ultrasonics and Optics for Neurotechnology Devices, Methods, and Applications," the entirety of each of which are incorporated herein by reference.

BACKGROUND OF THE INVENTION

1. Field of the Invention

The present invention is directed generally to GHz-THz ultrasonic and optic devices in neurotechnology and, more particularly, to a neuro-cognitive system for interrogating and actuating neural tissue.

2. Description of Related Art

How the brain works and how it computes is a grand challenge for humanity to solve. Understanding the mind, its structure, and function will help us explain and cure diseases, such as cancer, Alzheimer's, Parkinson's, and other neurogenerative disorders. The knowledge of how the brain works also helps understand how the brain can compute very complex tasks with excellent efficiency. Research in the last several decades has provided scientists with a good understanding of how neurons work, particularly at the levels of a single neuron or small number of neurons. With the help of MRI (magnetic resonance imaging), there is also some knowledge of brain activity over a large volume at the time scale of seconds to minutes. What is now needed is new technology to bridge the significant gap in understanding between microscopic interactions at the neuronal level and the macroscopic structures that perform complex computations.

Impact of neurotechnology for discovery and therapeutics is limited by two major challenges. One challenge is the failure of electrical neural interfaces over long term, and the other is the lack of technology for non-invasive, localized excitation of axons and neurons with 5-resolution for nerve activation and healing using stem cell therapies. Electrical interfaces consisting of electrodes that sample neuron generated potentials and currents are regularly used in research, some even with RF-powered and RF-data linked implantable systems have been developed. However, the neural probes do not last beyond a few weeks to a few months, as tissue buildup on the electrodes insulates the signal flow, even with capacitive readout. The tissue buildup also limits the lifetime over which the electrodes can be used to excite neurons and axons. Deep-brain passivated stimulator electrodes have to be replaced every few years with life threatening surgical procedures.

Recent advances in optical imaging and optogenetics has led to a revolution in being able to measure and excite neural signals using optical beams through optical windows into the brain, and is an excellent tool for scientific studies of how the brain works. However, these systems require high laser power, suffer from limitations due to phototoxicity and penetration depth, and cannot be totally packaged inside the brain. Furthermore, optogenetics requires genetic modifications of brain that could be a major barrier for translation to human treatment. Hence, measuring neural signals without electrode degradation and exciting specific neurons and axons, with a completely implantable and label-free system, remains an unsolved problem.

Therefore, there is a need for a device and system for interrogating and actuating neural tissue.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention are directed to a neuro-cognitive system for interrogating and actuating neural tissue. According to one aspect, the neuro-cognitive system includes a plurality of cognitive units and the cognitive units are connected. The system also includes a substrate having at least one surface and an electrode configured to detect an electrical output from at least one of the plurality of cognitive units. The system additionally includes a CMOS chip attached to the surface of the substrate and a plurality of transducers connected to the CMOS chip. Each of the plurality of transducers is configured to emit a phased ultrasonic beam which extends from the respective transducer toward the surface of the substrate.

According to another aspect, the present invention is a neuro-cognitive system. The system includes a plurality of cognitive units and the cognitive units are connected. The system also includes a CMOS chip having a top surface and a bottom surface, and a plurality of transducers connected to the CMOS chip. Each of the plurality of transducers is configured to emit an ultrasonic pulse to at least a portion of the plurality of cognitive units.

According to yet another aspect, the present invention is a method for reading an electrical output of one or more cognitive units. The method includes the steps of: (i) providing a neuro-cognitive system having a substrate with a top surface and a bottom surface, a microfluidic cavity within the top surface, an electrode extending into the microfluidic cavity, a CMOS chip attached to the bottom surface of the substrate, and a plurality of piezoelectric GHz transducers connected to the CMOS chip; (ii) placing one or more cognitive units into the microfluidic cavity, each of the one or more cognitive units having electrically excitable cells; (iii) emitting a phased ultrasonic beam from at least one of the plurality of piezoelectric GHz transducers, wherein the phased ultrasonic beam extends from the respective piezoelectric GHz transducer toward the top surface of the substrate; and (iv) detecting, via the electrode, the electrical output of at least one of the one or more cognitive units.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
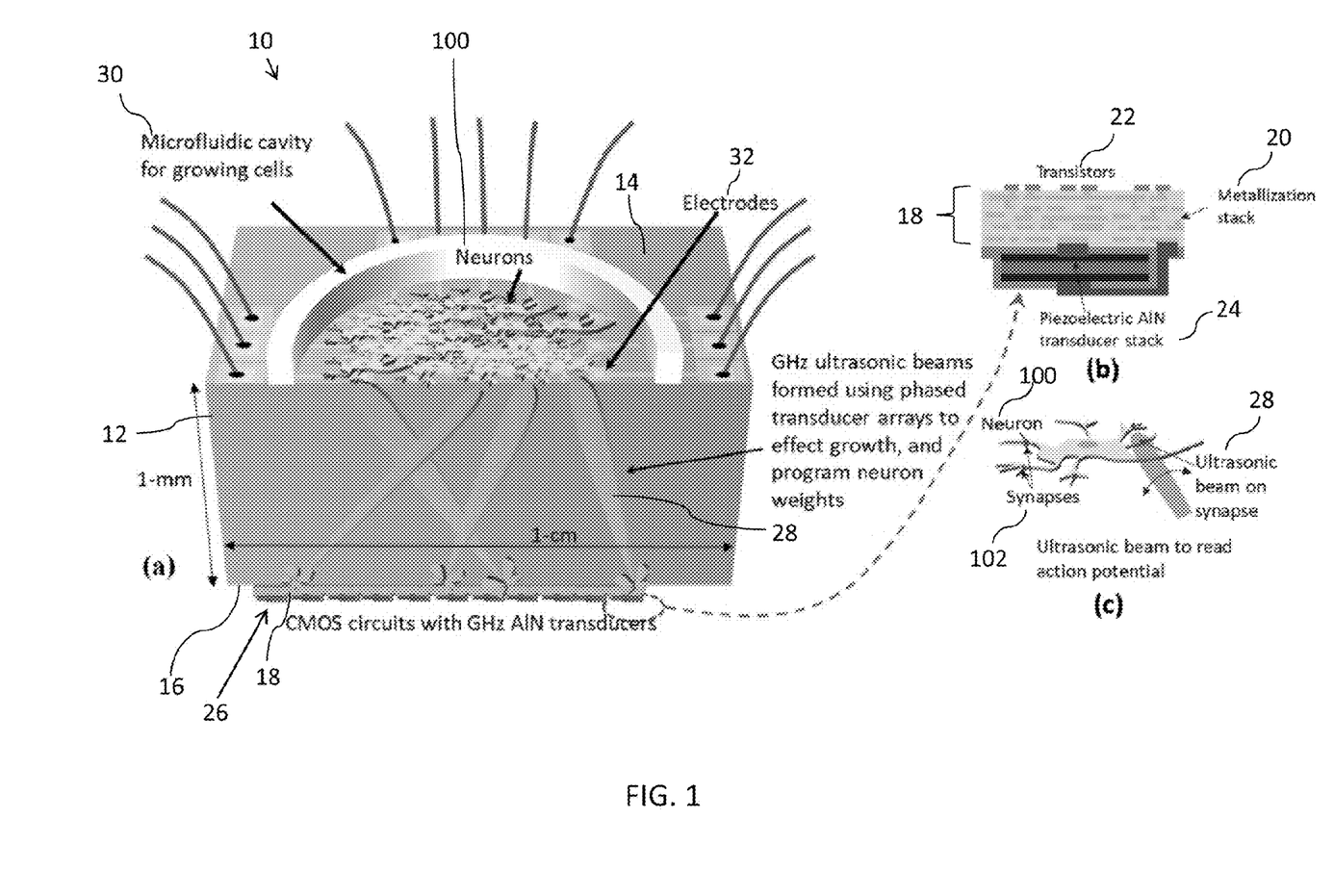
FIG. 1 is a perspective view schematic representation of a neuro-cognitive system, according to an embodiment.

Referring now to the figures, wherein like reference numerals refer to like parts throughout, FIG. 1 shows a perspective view schematic representation of a neuro-cognitive system 10, according to an embodiment. In the depicted embodiment, the neuro-cognitive system 10 is microscale, having the following dimensions: 1-cm×1-cm×1-mm volume. In other embodiments, the depth of the neuro-cognitive system 10 has a thickness of 10 µm to 10 mm, preferably 100 µm to 1 mm; the length and width of the neuro-cognitive system 10 is within the range of 0.1 mm to 20 mm, preferably 1 mm to 10 mm. The neuro-cognitive system 10 is a substrate 12 comprising a top surface 14 and a bottom surface 16. In an embodiment, the substrate 12 is composed of silicon.

The bottom surface 16 of the substrate 12 comprises a CMOS chip 18. In the preferred embodiment, the CMOS chip 18 has RF CMOS technology, which uses RF for external powering and communication by RF wireless interlinks. As shown in FIG. 1, the CMOS chip 18 includes a metallization stack 20 and one or most transistors 22. One or more piezoelectric thin film transducers 24 are connected to the metallization stack 20 of the CMOS chip 18. In the depicted embodiment, the transducers 24 are GHz AlN transducers. Specifically, the transducers 24 are AlN piezoelectric GHz phased transducers capable of generating GHz ultrasonic waves, which can be phased to form narrow beams. In an embodiment, the CMOS chip 18 has a thickness of ~500-700 µm, the thickness needed to allow beamforming to take place, which is enabled by the very low loss of GHz ultrasonic waves in a silicon substrate 12.

Figure 2:
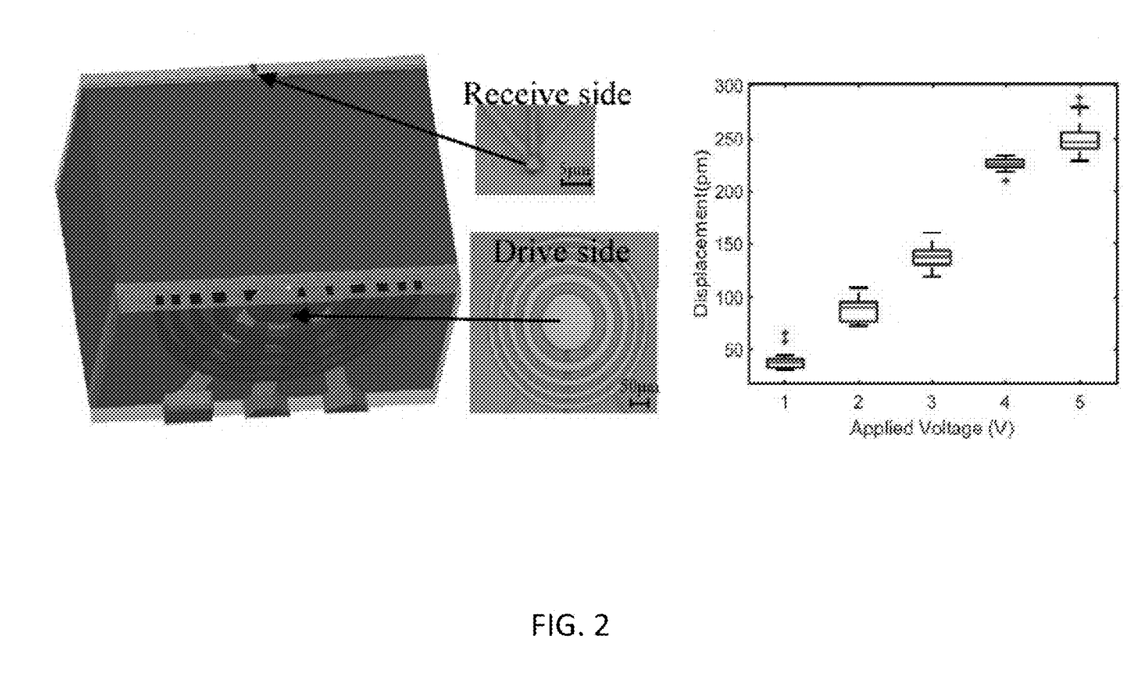
FIG. 2 is an exemplary fixed phase array.

Still referring to FIG. 1, each transducer 24 (e.g., piezoelectric AlN transducer stack) is connected to the metallization stack 20 of the CMOS chip 18. In the depicted embodiment, the transistors 22 of the CMOS chip 18 are attached to the bottom surface 16 of the substrate 12. Further, in the depicted embodiment, the plurality of transducers 24 are arranged in an array 26 on the CMOS chip 18. The CMOS integrated sonic transducer arrays 16 can be tiny, 100×100 to 1000×1000 µm transducers 16 on a chip 18, which is due to the small ultrasonic wavelength 9 µm at 1 GHz. The intensity of the pulse scales as $I=\frac{1}{2}\rho c(N^2 Q^2 \omega^2 V^2 d_{33}^2)$ where N is the number of elements, Q is that quality factor of each transducer 24 (~4-5 for low-Q operation), $\omega$ is the resonance frequency, V is the voltage and $d_{33}$ is the piezoelectric coefficient. By going to higher frequencies ($\omega$) in the above equation, one can achieve high intensities at much lower drive voltages. FIG. 2 demonstrates this with a fixed phase array. A set of AlN transducers formed in a Fresnel lens configuration was fabricated to focus the sonic field on the opposing side of the wafer, achieving intensities of 2000 w/cm$_2$. This is sufficient to tear apart and/or ablate neurons from the surface. Much lower intensities can be used to control the effect on synaptic strengths, as described below.

Referring back to FIG. 1 the transducer array 26 ultimately generates narrow, pencil-like ultrasonic beams 28. At 1-GHz frequency, the wavelength in a silicon substrate 12 is ~9 µm, with each pixel of an array being 4.5×4.5 µm. The ultrasonic beams 28 are emitted by the transducers 24 toward the top surface 14 of the substrate 12. As shown in FIG. 1, the top surface 14 of the substrate 12 comprises a microfluidic cavity 30. The purpose of the microfluidic cavity 30 is for growing cells. The system 10 also includes a plurality of electrodes 32. The electrodes 32 extend through the top surface 14 of the substrate 12. Specifically, the electrodes 32 are electrical pads extending into the microfluidic cavity 30. The electrical pads 32 are configured to read electrical output of objects in the microfluidic cavity 30. Objects for placement in the microfluidic cavity 30 have electrically excitable cells.

Still referring to FIG. 1, the objects in the microfluidic cavity 30 are cognitive units 100. A cognitive unit 100 can include a neuron, group of neurons, a nerve, group of nerves, and a node in a neural network. The cognitive units 100 can be connected to form a network. Each type of cognitive unit 100 is discussed below. In the embodiment shown in FIG. 1, each cognitive unit 100 is a neuron or a group (i.e., plurality) of neurons. Each neuron 100 includes one or more synapses 102. The transducer array 26 can be driven by <1V CMOS compatible voltage drive to achieve significant ultrasonic intensity to affect the neurons 100. In the depicted embodiment, the neurons 100 are scanned with the pencil-like GHz ultrasonic beam 28 from the transducer array 26 to excite the synapses 102, read cells, and form networks in the initial neural growth stage. The neurons 100 can also be read out using two-photon imaging.

Figure 3:
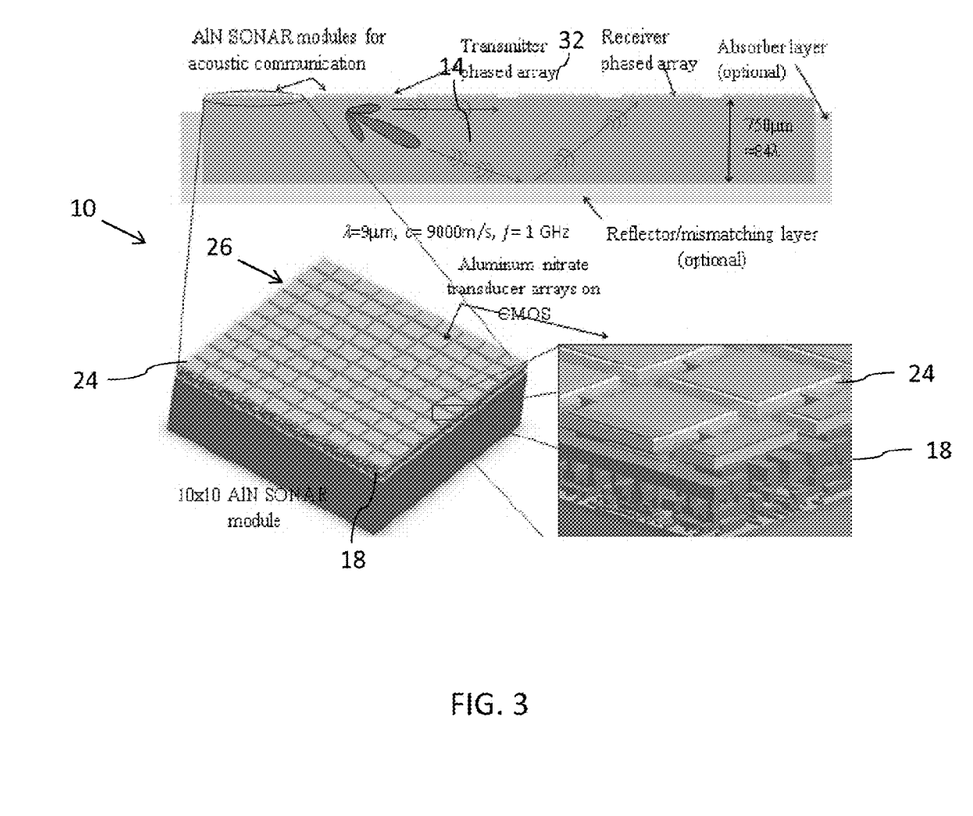
FIG. 3 is a perspective view schematic representation of a neuro-cognitive system, according to an alternative embodiment.

Turning now to FIG. 3, there is shown a perspective view schematic representation of a neuro-cognitive system 10, according to an alternative embodiment. In the depicted embodiment, a GHz AlN transducer 24 is integrated onto a CMOS chip 18 for sonic beam scanning with 1-5 um resolution. The CMOS chip 18 integrated with GHz sonic beam forming capabilities can interrogate and actuate neural tissue. As shown in FIG. 3, there is a 10×10 AlN array 26 of transducers 24 integrated on the CMOS chip 18. 1-5 GHz ultrasonic transducers 24 can be integrated with the CMOS chip 18 and piezoelectric thin films based on two scaling laws—(1) GHz to THz piezoelectric thin films can be integrated onto CMOS chips 18, and (2) the electronics needed to drive and sense the transducers 24 can be miniaturized and placed in the very same CMOS chips 18. This enables generating ultrasonic pulse packets for on-chip communications. Such pulses have been used to image fingerprints with a 20 μm resolution. Phased array operation allows less than 2 μm resolution beams with 1-volt CMOS compatible voltages.

Figure 4:
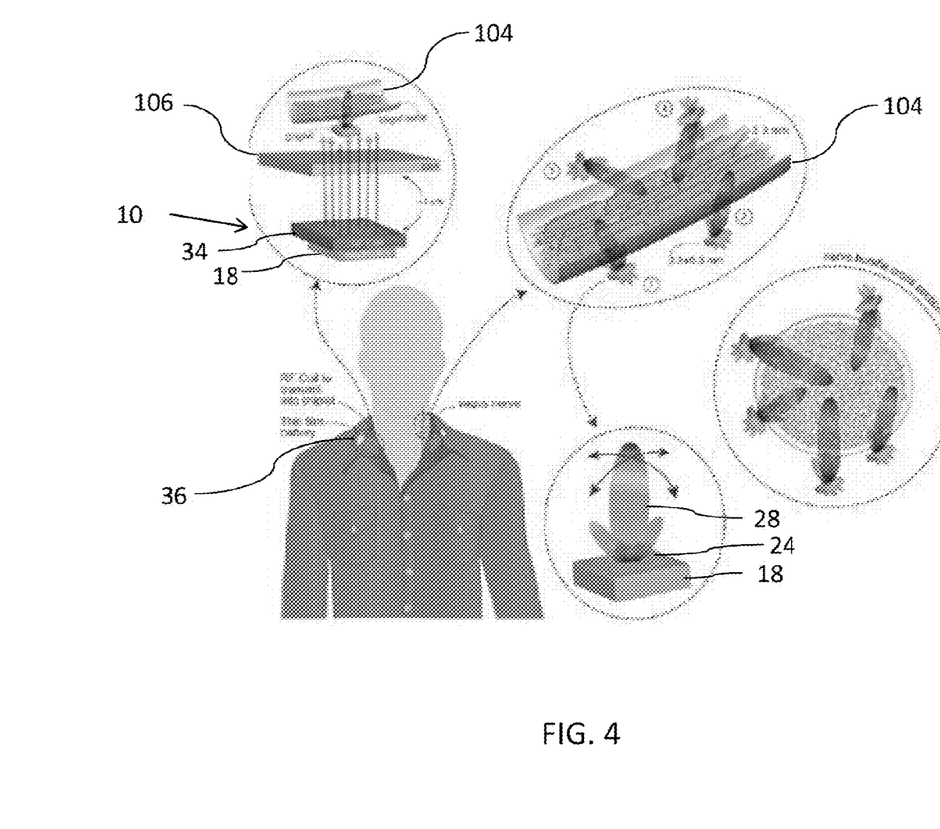
FIG. 4 is a perspective view schematic representation of the neuro-cognitive system of FIG. 3 positioned on a nerve, according to an embodiment.

Referring now to FIG. 4, there is shown the neuro-cognitive system 10 positioned on a cognitive unit 100, according to an embodiment. In the depicted embodiment, the cognitive unit 100 is a human nerve 104. The CMOS integrated sonic transducer arrays 26 can be tiny, 100×100 to 1000×1000 μm chips, and can consist of RF coils 34 to for external powering and communicate by RF wireless interlinks, as shown in FIG. 2. These CMOS chips 18 can be placed at different locations in tissue and be used to transmit and measure ultrasonic wave packets. In the depicted embodiment, a thin film battery 36 is wirelessly connected to the RF coil 34, powering the CMOS chip 18. The CMOS chip 18 is placed on or up to ~1 cm from the skin 106 near a nerve 104. Due to the GHz-THz ultrasonic capabilities of the transducers 24 on the CMOS chip 18, the absorption is high at such high frequencies, making fields penetrating only a few microns to even a few nanometers at THz. However, this feature can be used to confine the effects of the ultrasound to a small region near the transducer 24, which can be analyzed using optical imaging.

Thus, in both embodiments (FIGS. 1 and 3-4), the neuro-cognitive system 10 is a cyborg chip because it is part electronic, due to the CMOS chip 18, and part biological, due to the neurons 100. The purpose of the neuro-cognitive system 10 is to interrogate and actuate neural tissue. The system 10 can be used for cell growth control, neuromodulation, and using GHz ultrasonic beam 28 to extract action potentials on the top surface 14 and program synaptic weights. The data from the optics, electrodes, and ultrasonic pickups can be used to actuate and sense in the neural network formed by the neurons 100. With a sufficient number of ultrasonic pixels, the focal point of the beam 28 can be narrow enough to focus an effect specific section of a neuron 100 to enhance or decrease synaptic weights owing to ultrasonic radiation forces and acoustic streaming.

Figure 5:
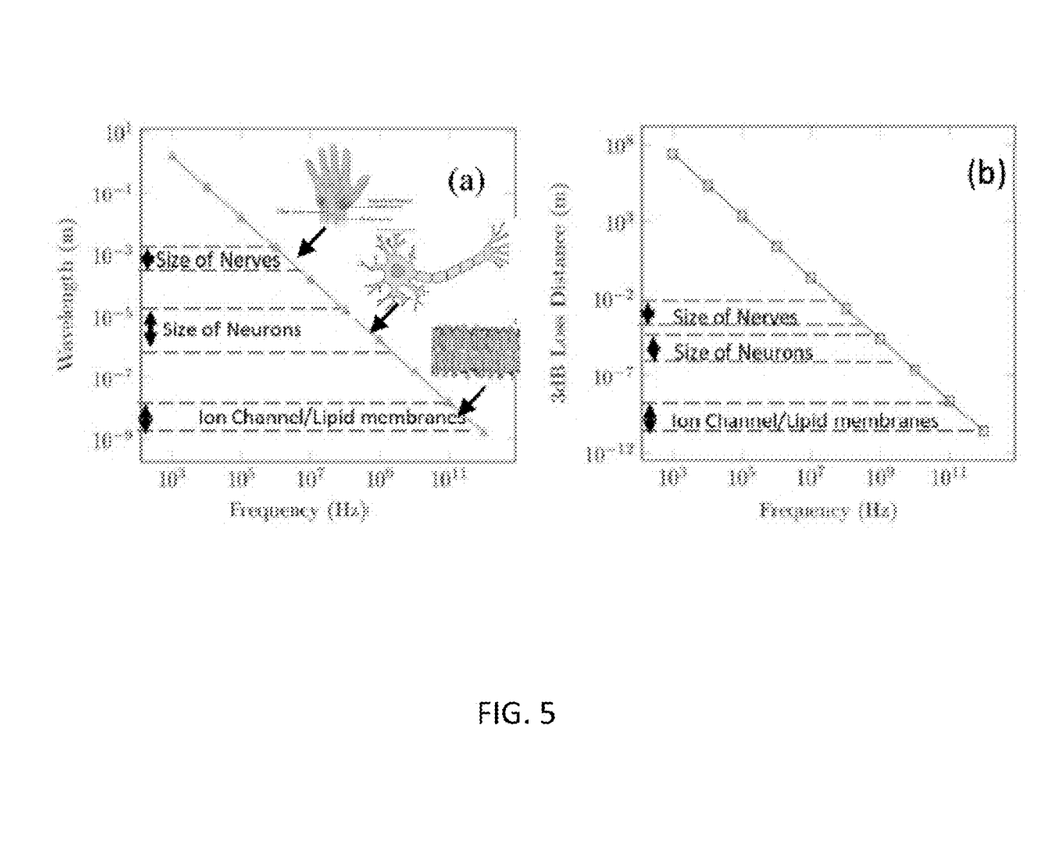
FIG. 5 shows graphs of the wavelength in water as a function of frequency and the 3 dB loss distance for ultrasonic plane waves as a function of frequency in water.

By operating at GHz frequencies, sonic beams 28 are formed with 2-5 μm focal points ~1-2 degree beam widths that can be used to interrogate and scan a neuron 100 such that specific sites of the neuron with specific synaptic connections can be exposed (FIG. 5). Furthermore, energy decay in water and tissue at GHz frequencies is very high, allowing one to confine the GHz energy to within a few neurons to 100s of microns at 100 MHz. Hence, 0.1-10 GHz ultrasonics provides a good mechanism to investigate the effects of ultrasonics on neural preparations, providing sub neuron addressing, and depth-confined effects. In some embodiments, the transducers 24 have a frequency within the range of 0.1 to 500 GHz, preferably 1 GHz to 200 GHz, or 10 GHz to 200 GHz. In some embodiment, the energy is confined to have a precise sonic energy with a frequency within the range of 0.01 GHz to 20 GHz, preferably 0.1 GHz to 10 GHz, when the emitted energy reaching the biological samples (connected cognitive units) after decay. By exposing neurons 100 to just precise sonic energy, one can custom engineer neural connectivity using conventional stimulation mechanisms. These mechanisms include radiation force, acoustic streaming, direct straining of ion-channels, and potentially heat. Short terms neuromodulation effects may lead to short term effects, while longer term exposures may lead to genetic changes for cell differentiation.

Figure 6:
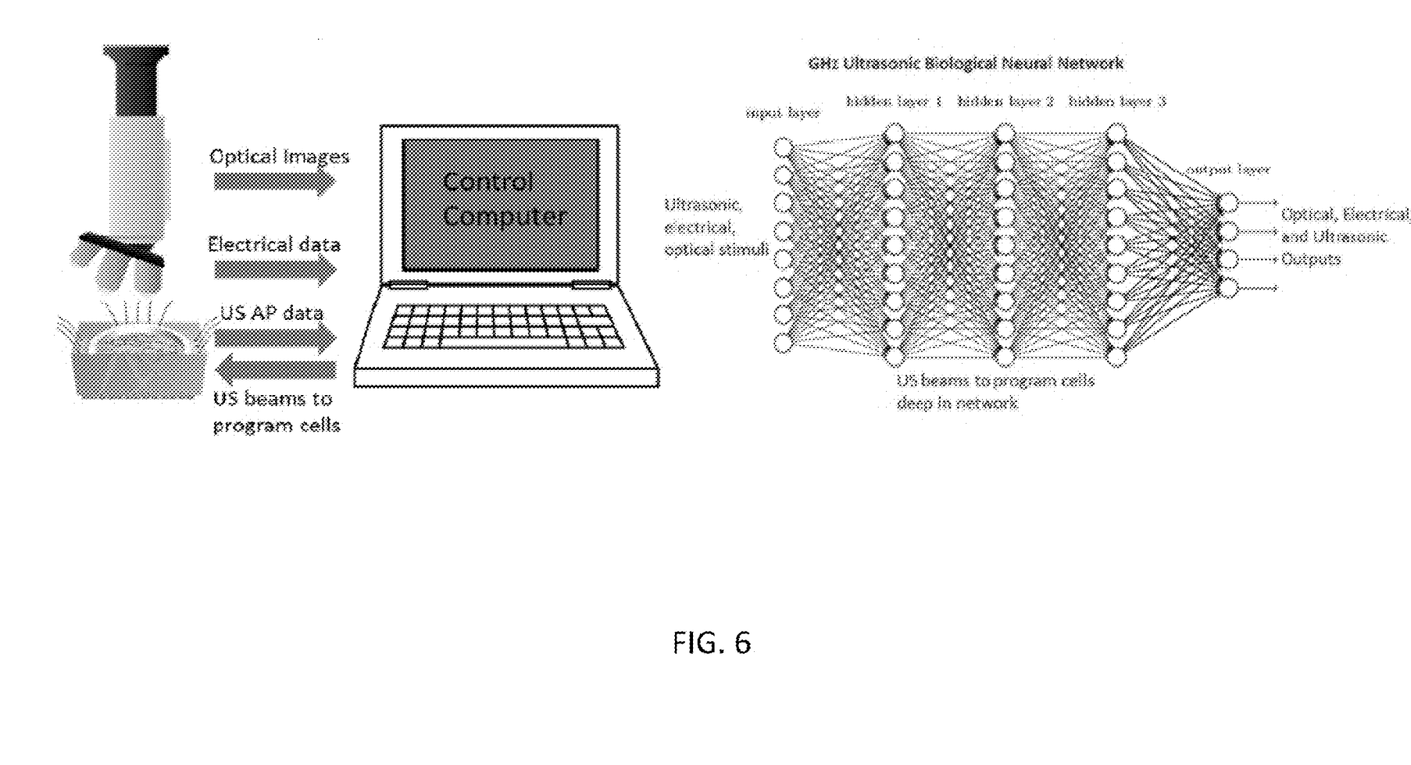
FIG. 6 is a diagram of data flow from the neuro-cognitive system to a control computer to create a neural network.
Figure 7:
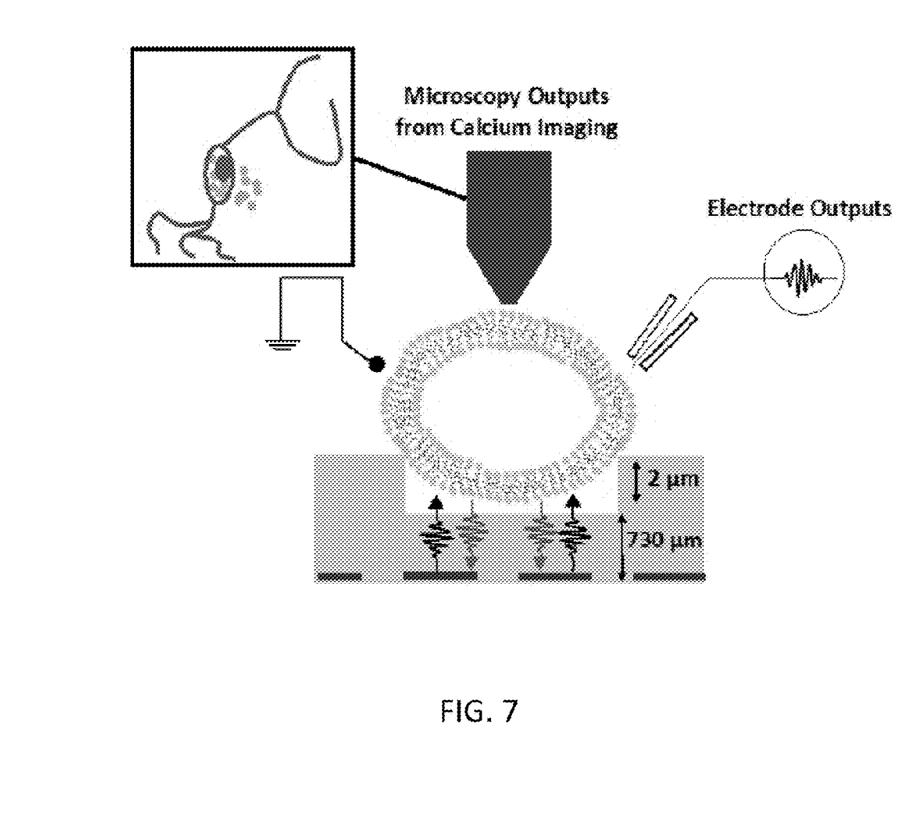
FIG. 7 is a diagram of a GHz sonar integrated onto CMOS for sonic beam scanning with 5-10 µm resolution.

The system 100 in FIG. 1 can be used to form a desired network of cells, and then adjust synaptic weights between the connections of the cell network. Further, the system in FIG. 1 can consist of thousands to millions of neurons 100 with 100-1000 synapses 102 per neuron 100. The multi-dimensional inputs from optics, electrical readouts from the cells, and ultrasonic readouts form a large class of inputs that can be used to learn the variables of the neural network formed by the neural volume controlled by ultrasonic waves, as shown in FIG. 6. The neural network is composed of a plurality of cognitive units. In the embodiment of FIG. 6, each cognitive unit is a node in the neural network. In FIG. 6 (left), optical data from imaging the top, electrical data, and ultrasonically measured potentials can be used to program the neural computing by adjusting the synaptic weights, and cell differentiation using the GHz sonic beams 28. For example, data from optical imaging is transmitted to a control computer for use in creating a neural network and programming for cells. In FIG. 6 (right), there is a multi-level deep neural network implemented using the multiple inputs and outputs applied to the brain-on-chip system 10, shown in FIG. 1.

In an embodiment, a back-propagation or back-propagation like algorithm is implemented to program a biological neural network. The purpose of programing the system 10 is to make the system 10 generate a desired output neural activation (at pre-established output neurons) in response to a set of input stimuli. The electrical, optical, and ultrasonic data (received from ultrasonic reflected signals scanned over the neural formed layer to the silicon surface with incident sonic waves) will be interpreted by the computer program, which will in turn establish an ultrasonic beam protocol that will modify the weights to reduce the difference between present output and desired output.

Figure 8:
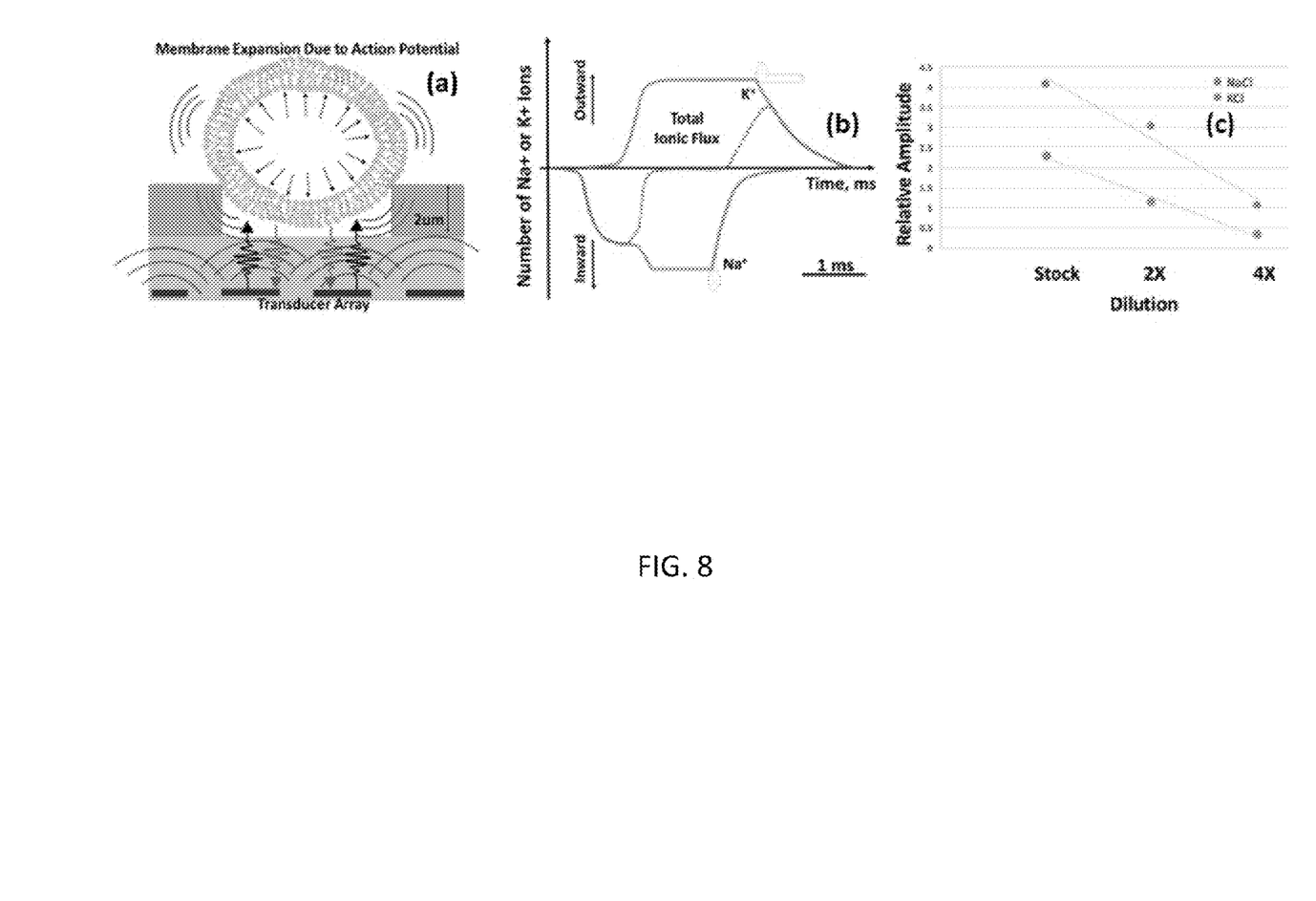
FIG. 8 is a diagram of expansion of a neuron membrane due to action potential and graphs of Na+ and K+ ion variation and the resulting acoustic signals.

In an embodiment for a method for stimulating, differentiating, positioning, and reading signals from neural cells, ultrasonic and acoustics are used with optical verification. Axons and neurons 100 will be placed on a surface 14 of a chip 18 with AlN (Aluminum nitride) piezoelectric thin film transducer arrays 26 (with high frequencies in the 100-200 GHz range), as shown in FIG. 8. The setup enables electrical isolation from the biological sample (e.g., neurons 100), connected only by the ultrasonic links from one surface 14 of the chip 18 to the opposite surface 16. This enables the surface 14 facing the tissue to be independent of electrical interfaces that age over time. The piezoelectric transducers 24 generate sonic pulses, 50-70 ns in time duration, consisting of 30-40 1.3 GHz cycles. These pulses travel to the silicon substrate 12 and return back modified by the surface 14 reflection and absorption.

The neurons 100 and related axons are monitored optically on the top surface 14 of the ultrasonic chips 18, while the ultrasonic and acoustic transducers 24 will be used to scan the surface 14 from the backside (or bottom surface 16). To quantify neural measurements and modulation, optical imaging is used, such as optical imaging of ion channel firing using optical labels, such Ca+ specific dyes. Other optical tools known in neural imaging can be used to image both single cell layers and tissue slices of up to 100-300 µm using two photon imaging.

Figure 9:
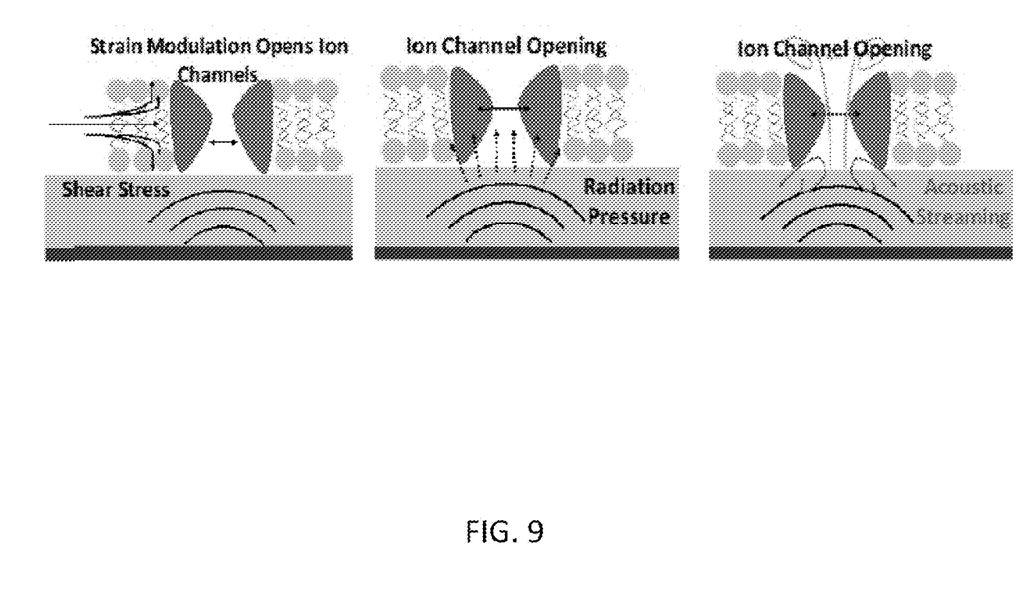
FIG. 9 is a series of diagrams showing direction strain activation, radiation force, and acoustic streaming.

The amplitude and phase of the return ultrasonic pulses from the neurons 100 will be used to detect action potential over a long time. Physical approaches include: (a) The neuron mass density variations and rigidity of the axons wall will generate sufficient ultrasonic impedance contrast to detect the cell on the transducers 24, as shown in FIG. 9. The expansion and contraction of the neurons 100 would lead to changes in the surface boundary conditions in terms of increased contact area between the cells and the sensor surface 14, and the applied pressure onto the surface 14. The outputs of the ultrasonic imaging of neurons 100 will provide initial results necessary to show acoustic readout of action potentials using the theory of acoustic wave propagation associated with action potentials; (b) The variation of Na+ and K+ concentrations can change between 5-50 m Mol concentrations in small confined volumes, which can occur between neurons 100 and sensor surface 14, as shown in FIG. 9. In preliminary data, shown in FIG. 9, ultrasonic absorption due to ion concentration changes can be detected using GHz sonic pulse reflections, as suggested by similar results of sonic absorption in sea-water; (c) The acoustic signals emitted from neurons 100 as pressure waves can be used to modify surfaces or actuate thin piezoelectric thin films transducers 24 with gaps to detect kHz signals. For this the AlN transducers 24 will be formed on thin membranes that act as microphones to detect sound generated by the neuron 100.

Regarding neuromodulation, one or more GHz ultrasonic pixels can be phased in a way to add coherently on the tissue side such that the intensity of the ultrasound is enough to trigger effects that lead to neuromodulation. The acoustic intensity can be written as $I = \rho c v_p^2 = \rho c \omega^2 u_p^2$ where ρ is the density of water (~1000 kg/m$^3$), c is the speed of sound (~1500 m/s), $v_p$ is the peak particle velocity, which is equal to $\omega^2 u_p^2$ where ω is the angular frequency, and $u_p$ is the peak displacement of the sonic pulse. The peak displacement of a sonic pulse excited by one of the transducers can be estimated to be $d_{33}V$ where $d_{33}$ is the piezoelectric coefficient and V is the applied voltage, which is typically in the 1 to 3 volts range for CMOS compatibility. For N transducer phased to add up coherently in water, and assuming a focal point of approximately a wavelength, we estimate the strain in water to be $$\epsilon = \frac{2\pi N d_{33} V f}{c_{sound}}$$

which is ~60*10$^{-6}$ for 1 GHz and one AlN transducer (N=1, $d_{33}$~6*10$^{-12}$C/N).

Mechanically induced strain on cellular membranes have been known to induce ion channel activation at 10-50µ-strain, indicating that there should be effects of the sonic beam on membrane ion channels seen. Since this strain is at a high frequency, and the mechanisms of the ion channels are likely to be nonlinear functions of applied strain owing to configurations of protein sub-assemblies that have non-linear properties, the AC strain field is likely to be rectified to produce observable effects. In addition to direct strain, there may also be effects of radiation force, acoustic streaming. The radiation force $$F = \frac{2\alpha I}{c} (\alpha = \text{absorption coefficient})$$

can be very high owing to high absorption at GHz frequencies. Related to acoustic radiation forces is acoustic streaming induced by gradients in radiation forces that can excite fluid flow vortices, which in turn can cause shear stresses. In order to quantify the effect on modulation of action potential generation, optical measurements are relied on to independently verify action potentials. Optical Ca$^{2+}$ imaging will be used to measure the neural activity timed with US pulse excitation. The neural activity modulation will be quantified by varying the sonic field and frequency and correlating electrical, ultrasonic execution to electrical excitation. We plan on using an in vitro system that will allow us to characterize neuromodulation on the cellular level and build this up to a 3D cell culture system to show that we can localize effects of ultrasonic stimulation at varying depths from the transducer, using both multi-photon Ca$^{2+}$ imaging and electrode arrays with the ability to obtain readings from several micrometers in depth. In some embodiments, the depth is within the range of 1 to 1000 micrometers.

Regarding cell differentiation using ultrasonic forces, ultrasonic beams 28 can induce radiation forces and acoustic streaming on the transducer surface that can apply time-averaged DC mechanical stimuli to cells. GHz ultrasonic with smaller wavelengths will enable very tightly focused beams for excitation of cells at specific location enabling identification of mechanisms. It has been shown that the mechanical forces transmitted through the cells walls can activate proteins that can affect the nucleus by mechanical adhesion and pulling forces. Stem cells can be isolated from a cell culture using this technique of isolating cells via differences in cellular mechanics. Ultrasonics modifies surface adhesion in addition to forces on cells, as many studies have shown cells collecting at nodes of standing sonic waves. Stem cells that produce neural blastomas will be exposed to ultrasonic fields and be optically imaged for differentiation. There is the possibility for differentiation of cells and also the ability to distinguish the stage of differentiation of a cell using GHz ultrasonic exposure. Therefore, the experimental design takes place in two parts.

The first set of experiments being whether the interaction of cells with substrate can be detected, and subsequently biomechanics, using ultrasonic stimulation. The second part of experimentation will be to determine, using this biomechanics data, whether a cell has been differentiated after exposure to ultrasound. Cellular biomechanics has been investigated for a long time by using substrate interactions, a variety of force microscopy techniques, and optical trapping. Previous studies have shown the use of ultrasonics to create acoustic tweezers that can be used to deduce cellular forces. Using a similar approach, data can obtained that quantifies cellular response to ultrasonics, and by extension cellular mechanics, using optical techniques to connect this to differentiation. Then, on longer time scale, cells can be influenced with ultrasound and deduce whether cells can be differentiated, and do so in a localized manner, creating microenvironments of differentiated cells without having to rely heavily on microfluidics, much like many other studies that show in vitro differentiation and tissue engineering with complex structures defining differentiation factor compartments. In addition to this one mechanism of ultrasonic differentiation, ultrasound has been shown to influence cellular uptake, which means that cells influenced by ultrasound, due to similar mechanisms presented in FIG. 10, are likely to endocytose differentiation factors with a higher probability.

To base the observed results on hypothesis based on physical principles, and to explain phenomenological observations, analytical and COMSOL based finite element models of the transducers and interactions with biological tissue can be developed. FEM models of ion channels embedded in membranes will be simulated in COMSOL using nonlinear material models corresponding to those of tissue like materials. The sonic fields will interact with the models to allow computational verification of strain generated, radiation force, and acoustic streaming based on the velocity fields extracted from COMSOL. The FEM results can be verified from first order analytical models of ultrasonic absorption and field distribution based on piston models of the transducer in the fluids with varying degree of random heterogeneity owing to neurons distributed within tissue.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A neuro-cognitive system, comprising:
    an implantable device, the implantable device including:
        a substrate having a first surface and a second surface opposite the first surface;
        a cellular interaction region disposed at or in the first surface of the substrate;
        an electrode electrically connected to the cellular interaction region; and
        a CMOS chip, comprising a plurality of transducers, attached to the second surface of the substrate wherein the plurality of transducers comprise a first plurality of transducers configured to transmit phased ultrasonic beams through the substrate toward the cellular interaction region to interrogate, to impart energy to, or to activate, in vivo, one or more cells or one or more biological structures at or adjacent the cellular interaction region and wherein the plurality of transducers further comprise a second plurality of transducers configured to receive return signals from the one or more cells or one or more biological structures at or adjacent the cellular interaction region responsive to the transmitted phased ultrasonic beams.

2. The system of claim 1, wherein each of the plurality of transducers is configured to operate at a frequency between 0.1 GHz and 200 GHz and to output a phased ultrasonic beam having a 2-5 µm focal point.

3. The system of claim 1, wherein the cellular interaction region comprises a microfluidic cavity configured to receive one or more cells or one or more biological structures.

4. The system of claim 1, wherein at least some of the plurality of transducers comprise a piezoelectric GHz AlN transducer stack.

5. The system of claim 1, wherein at least some of the plurality of transducers are configured to output pulsed beams between 50-70 ns in duration.

6. The system of claim 1, wherein the CMOS chip comprises a metallization stack to which the plurality of transistors are attached.

7. The system of claim 1, wherein the CMOS chip comprises a radio frequency (RF) coil configured to transmit at least one of power and data.

8. The system of claim 1, wherein the cellular interaction region comprises a plurality of cellular interaction regions, wherein the electrode electrically connected to the cellular interaction region comprises an electrode connected to each of the plurality of cellular interaction regions, and wherein each of the first plurality of transducers are selectable to emit phased ultrasonic beams through the substrate toward the cellular interaction regions to interrogate, to impart energy to, or to activate a selected cell, plurality of cells, structure, or plurality of structures at or adjacent each of the plurality of the cellular interaction regions, wherein the selected cell, plurality of cells, structure, or plurality of structures comprises one or more cells, tissue, one or more nerve fibers, one or more axons, or one or more neurons.

9. The system of claim 1, wherein the substrate has a thickness within a range of 0.1 to 1 mm, wherein the CMOS chip comprises a thickness within a range of 500 to 700 µm, or wherein the substrate has a thickness within a range of 0.1 to 1 mm and the CMOS chip comprises a thickness within a range of 500 to 700 µm.

10. The system of claim 1, wherein the plurality of transducers are configured to emit the phased ultrasonic beams at a frequency, duration and/or energy to induce strain on cellular membranes of the one or more cells or one or more biological structures at or adjacent the cellular interaction region sufficient to induce ion channel activation in the one or more cells or one or more biological structures.

11. The system of claim 1, further comprising an RF wireless device operatively associated with the in vivo CMOS chip and an ex vivo external controller, wherein the RF wireless device is configured to output the return signals received by the in vivo CMOS chip to the ex vivo external controller configured to process the return signals and to transmit control signals to the in vivo CMOS chip via the RF wireless device.

12. A neuro-cognitive system, comprising:
an implantable device, the implantable device including:
a substrate having a first surface and a second surface opposite the first surface;
a cellular interaction region disposed at or in the first surface of the substrate;
a CMOS chip disposed adjacent the second surface of the substrate, the CMOS chip comprising a plurality of transducers, the plurality of transducers comprising a first plurality of transducers to transmit phased ultrasonic beams through the substrate toward the cellular interaction region to interrogate, to impart energy to, or to activate, in vivo, one or more cells or one or more biological structures at or adjacent the cellular interaction region and further comprising a second plurality of transducers to receive return signals from the one or more cells or one or more biological structures at or adjacent the cellular interaction region responsive to the transmitted phased ultrasonic beams; and
an electrode electrically connected to the cellular interaction region.

13. The system of claim 12, wherein at least some of the plurality of transducers are configured to operate at a frequency within the 1 GHz to 200 GHz range.

14. The system of claim 12, wherein at least some of the plurality of transducers are configured to transmit phased ultrasonic beams through the substrate toward the cellular interaction region and to receive return signals from the one or more cells or one or more biological structures at or adjacent the cellular interaction region.

15. The system of claim 12, further comprising a radio frequency (RF) coil connected to the CMOS chip.

16. The system of claim 12, wherein the cellular interaction region comprises a plurality of cellular interaction regions, wherein the electrode electrically connected to the cellular interaction region comprises an electrode connected to each of the plurality of cellular interaction regions, and wherein each of the first plurality of transducers are selectable to emit phased ultrasonic beams through the substrate toward the cellular interaction regions to interrogate, to impart energy to, or to activate a selected cell, plurality of cells, structure, or plurality of structures at or adjacent each of the plurality of the cellular interaction regions, wherein the selected cell, plurality of cells, structure, or plurality of structures comprises one or more cells, tissue, one or more nerve fibers, one or more axons, or one or more neurons.

17. A method for reading an electrical output of one or more cellular interaction regions of one or more implantable devices, comprising the steps of:
disposing a signaling unit comprising a first wireless communication device adjacent the skin of a subject within a wireless coupling range of a second wireless communication device of a first implanted implantable device of the one or more implanted implantable devices, the first implanted implantable device comprising the second wireless communication device, a substrate having a first surface and a second surface opposite the first surface, a cellular interaction region disposed at or in the first surface of the substrate, an electrode electrically connected to the cellular interaction region, a CMOS chip disposed adjacent the second surface of the substrate, the CMOS chip comprising a plurality of transducers, the plurality of transducers comprising a first plurality of transducers configured to transmit phased ultrasonic pulses with a frequency between about 1-200 GHz through the substrate toward the cellular interaction region of the first implanted implantable device to interrogate, to impart energy to, or to activate or more cells or one or more biological structures at or adjacent the cellular interaction region and further comprising a second plurality of transducers configured to receive return signals from the one or more cells or one or more biological structures at or adjacent the cellular interaction region responsive to the transmitted phased ultrasonic pulses;
wirelessly connecting the first wireless communication device of the signaling unit to the second wireless communication device of the first implanted implantable device; and
outputting a signal from the first wireless communication device of the signaling unit to the second wireless communication device of the first implanted implantable device to cause one or more of the plurality of transducers of the CMOS chip to output one or more ultrasonic pulses with a frequency between about 1-200 GHz toward the cellular interaction region of the first implanted implantable device.

18. The method of claim 17, further comprising the steps of:
disposing the signaling unit adjacent the skin of a subject within a wireless coupling range of a third wireless communication device of a second implanted implantable device of the one or more implanted implantable device, the second implanted implantable device comprising the third wireless communication device, a substrate having a first surface and a second surface opposite the first surface, a cellular interaction region disposed at or in the first surface of the substrate, an electrode electrically connected to the cellular interaction region, a CMOS chip disposed adjacent the second surface of the substrate, the CMOS chip comprising a plurality of transducers configured to emit ultrasonic pulses with a frequency between about 1-200 GHz through the substrate toward the cellular interaction region to interrogate a cell or a plurality of cells at or adjacent the cellular interaction region or to impart energy to a cell or a plurality of cells at or adjacent the cellular interaction region;

wirelessly connecting the first wireless communication device of the signaling unit to the third wireless communication device of the second implanted implantable device; and outputting a signal from the first wireless communication device of the signaling unit to the third wireless communication device of the second implanted implantable device to cause one or more of the plurality of transducers of the CMOS chip to output one or more ultrasonic pulses with a frequency between about 1-200 GHz toward the cellular interaction region of the second implanted implantable device.

19. The method of claim 17, wherein the first wireless communication device and the second wireless communication device comprise radio frequency (RF) devices.

20. The method of claim 17, further comprising:

outputting the return signals received by the CMOS chip of the first implanted implantable device to the external signaling unit; and transmitting control signals to the CMOS chip of the first implanted implantable device via the external signaling unit.

21. The method of claim 20, further comprising:

processing the return signals in the external signaling unit or in an external controller to determine at least one characteristic of the return signals, wherein the transmitting of control signals to the CMOS chip of the first implanted implantable device is responsive to the determined at least one characteristic of the return signals, and wherein the control signals cause the first plurality of transducers of the CMOS chip of the first implanted implantable device to transmit phased ultrasonic pulses having at least one characteristic different than characteristics of the phased ultrasonic pulses associated with the return signals.

22. The system of claim 11, wherein the ex vivo external controller is further configured, responsive to a determined characteristic of the return signals, to transmit a control signal to the in vivo CMOS chip, via the RF wireless device, to cause the first plurality of transducers of the in vivo CMOS chip to transmit phased ultrasonic beams having at least one characteristic different than characteristics of the phased ultrasonic beams associated with the return signals.

* * * * *